United States Patent
Thorne

US007718616B2

(10) Patent No.: US 7,718,616 B2
(45) Date of Patent: May 18, 2010

(54) BONE GROWTH PARTICLES AND OSTEOINDUCTIVE COMPOSITION THEREOF

(75) Inventor: Kevin J. Thorne, Austin, TX (US)

(73) Assignee: Zimmer Orthobiologics, Inc., Austin, TX (US)

( * ) Notice: Subject to any disclaimer, the term of this patent is extended or adjusted under 35 U.S.C. 154(b) by 0 days.

(21) Appl. No.: 11/614,422

(22) Filed: Dec. 21, 2006

(65) Prior Publication Data

US 2008/0152687 A1 Jun. 26, 2008

(51) Int. Cl.
*A61K 8/65* (2006.01)
*C07K 14/78* (2006.01)

(52) U.S. Cl. .................... 514/12; 424/423; 424/489; 530/356

(58) Field of Classification Search ................ 530/356; 514/2, 12, 8, 54; 424/602, 488, 489, 490, 424/497, 423; 536/551
See application file for complete search history.

(56) References Cited

U.S. PATENT DOCUMENTS

| | | |
|---|---|---|
| 3,949,073 A | 4/1976 | Daniels et al. |
| 3,968,567 A | 7/1976 | Nevins |
| 4,131,597 A | 12/1978 | Bluethgen et al. |
| 4,191,747 A | 3/1980 | Scheicher |
| 4,192,021 A | 3/1980 | Deibig et al. |
| 4,202,055 A | 5/1980 | Reiner et al. |
| 4,233,360 A | 11/1980 | Luck et al. |
| 4,237,559 A | 12/1980 | Borom |
| 4,356,572 A | 11/1982 | Guillemin et al. |
| 4,394,370 A | 7/1983 | Jefferies |
| 4,412,947 A | 11/1983 | Cioca |
| 4,429,691 A | 2/1984 | Niwa et al. |
| 4,497,075 A | 2/1985 | Niwa et al. |
| 4,563,350 A | 1/1986 | Nathan et al. |
| 4,596,574 A | 6/1986 | Urist |
| 4,606,910 A | 8/1986 | Sawyer |
| 4,619,655 A | 10/1986 | Hanker et al. |
| 4,620,327 A | 11/1986 | Caplan et al. |
| 4,623,553 A | 11/1986 | Ries et al. |
| 4,629,464 A | 12/1986 | Takata et al. |
| 4,642,120 A | 2/1987 | Nevo et al. |
| 4,668,295 A | 5/1987 | Bajpai |
| 4,693,986 A | 9/1987 | Vit et al. |
| 4,698,326 A | 10/1987 | Sauk et al. |
| 4,774,227 A | 9/1988 | Piez et al. |
| 4,776,890 A | 10/1988 | Chu |
| 4,780,450 A | 10/1988 | Sauk et al. |
| 4,789,663 A | 12/1988 | Wallace et al. |
| 4,795,467 A | 1/1989 | Piez et al. |
| 4,843,112 A | 6/1989 | Gerhart et al. |
| 4,846,838 A | 7/1989 | Takai et al. |
| 4,863,732 A | 9/1989 | Nathan et al. |
| 4,863,856 A | 9/1989 | Dean, Jr. et al. |
| 4,888,366 A | 12/1989 | Chu et al. |
| 4,891,359 A | 1/1990 | Saferstein et al. |
| 4,950,483 A | 8/1990 | Ksander et al. |
| 4,970,298 A | 11/1990 | Silver et al. |
| 4,992,226 A | 2/1991 | Piez et al. |
| 5,001,169 A | 3/1991 | Nathan et al. |
| 5,024,841 A | 6/1991 | Chu et al. |
| 5,035,715 A | 7/1991 | Smestad et al. |
| 5,053,212 A | 10/1991 | Constantz et al. |
| 5,073,373 A | 12/1991 | O'Leary et al. |
| 5,085,861 A | 2/1992 | Gerhart et al. |
| 5,123,925 A | 6/1992 | Smestad et al. |
| 5,137,534 A | 8/1992 | Sumita |
| 5,152,836 A | 10/1992 | Hirano et al. |
| 5,154,931 A | 10/1992 | Kruger et al. |
| 5,162,114 A | 11/1992 | Kuberasampath et al. |
| 5,171,574 A | 12/1992 | Kuberasampath et al. |
| 5,204,382 A | 4/1993 | Wallace et al. |
| 5,207,710 A | 5/1993 | Chu et al. |
| 5,231,169 A | 7/1993 | Constantz et al. |
| 5,236,704 A | 8/1993 | Fujioka et al. |
| 5,246,457 A | 9/1993 | Piez et al. |
| 5,258,029 A | 11/1993 | Chu et al. |
| 5,262,166 A | 11/1993 | Liu et al. |

(Continued)

FOREIGN PATENT DOCUMENTS

EP 0164483 A1 6/1984

(Continued)

OTHER PUBLICATIONS

Kubler, N. et al., "Bone Morphogenetic Protein-Mediated interaction of Periosteum and Diaphysis: Citric Acid and Other Factors Influencing the Generation of Parosteal Bone", Clinical Orthopaedics and Related Research, No. 258, Sep. 1990, pp. 279-294.

(Continued)

*Primary Examiner*—Chih-Min Kam
(74) *Attorney, Agent, or Firm*—Howrey LLP

(57) ABSTRACT

A biocompatible synthetic bone growth composition comprising a fibrillar collagen component and a calcium phosphate component. The composition is formed into particles, and then formed into a unitary article that may be provided at the site of a skeletal defect. An osteoinductive component may be further added, either before or after forming the unitary article. The composition may be formulated as a paste or putty and facilitates bone growth and/or repair.

14 Claims, 1 Drawing Sheet

U.S. PATENT DOCUMENTS

| | | |
|---|---|---|
| 5,304,577 A | 4/1994 | Nagata et al. |
| 5,306,303 A | 4/1994 | Lynch |
| 5,320,844 A | 6/1994 | Liu |
| 5,338,772 A | 8/1994 | Bauer et al. |
| 5,352,715 A | 10/1994 | Wallace et al. |
| 5,356,629 A | 10/1994 | Sander et al. |
| 5,364,839 A * | 11/1994 | Gerhart et al. .............. 514/12 |
| 5,366,508 A | 11/1994 | Brekke |
| 5,399,361 A | 3/1995 | Song et al. |
| 5,422,340 A | 6/1995 | Ammann et al. |
| 5,425,770 A | 6/1995 | Piez et al. |
| 5,433,751 A | 7/1995 | Christel et al. |
| 5,443,531 A | 8/1995 | Ripamonti |
| 5,455,231 A | 10/1995 | Constantz et al. |
| 5,508,267 A | 4/1996 | Czernuszka et al. |
| 5,522,893 A | 6/1996 | Chow et al. |
| 5,522,894 A | 6/1996 | Draenert |
| 5,531,791 A | 7/1996 | Wolfinbarger, Jr. |
| 5,532,217 A | 7/1996 | Silver et al. |
| 5,549,671 A * | 8/1996 | Waybright et al. ............ 623/8 |
| 5,552,454 A | 9/1996 | Kretschmann et al. |
| 5,573,771 A | 11/1996 | Geistlich et al. |
| 5,618,339 A | 4/1997 | Ito |
| 5,645,591 A | 7/1997 | Kuberasampath et al. |
| 5,650,176 A | 7/1997 | Lee et al. |
| 5,677,284 A | 10/1997 | Li |
| 5,681,873 A | 10/1997 | Norton et al. |
| 5,683,461 A | 11/1997 | Lee et al. |
| 5,707,962 A | 1/1998 | Chen et al. |
| 5,709,934 A | 1/1998 | Bell et al. |
| 5,711,957 A | 1/1998 | Patat et al. |
| 5,739,286 A | 4/1998 | Silver et al. |
| 5,741,329 A | 4/1998 | Agrawal et al. |
| 5,755,792 A | 5/1998 | Brekke |
| 5,769,895 A | 6/1998 | Ripamonti |
| 5,769,897 A | 6/1998 | Harle |
| 5,776,193 A | 7/1998 | Kwan et al. |
| 5,824,087 A | 10/1998 | Aspden et al. |
| 5,830,493 A | 11/1998 | Yokota et al. |
| 5,837,752 A | 11/1998 | Shastri et al. |
| 5,846,312 A | 12/1998 | Ison et al. |
| 5,904,718 A | 5/1999 | Jefferies |
| 5,910,315 A | 6/1999 | Stevenson et al. |
| 5,932,207 A | 8/1999 | Schmidt |
| 5,948,426 A | 9/1999 | Jefferies |
| 5,952,010 A | 9/1999 | Constantz |
| 5,955,438 A | 9/1999 | Pitaru et al. |
| 5,958,430 A | 9/1999 | Campbell et al. |
| 5,964,805 A | 10/1999 | Stone |
| 5,990,381 A | 11/1999 | Nishihara |
| 5,997,895 A | 12/1999 | Narotam et al. |
| 6,013,853 A | 1/2000 | Athanaslou et al. |
| 6,013,856 A | 1/2000 | Tucker et al. |
| 6,027,742 A | 2/2000 | Lee et al. |
| 6,028,242 A | 2/2000 | Tucker et al. |
| 6,037,519 A | 3/2000 | McKay |
| 6,077,988 A | 6/2000 | Kuberasampath et al. |
| 6,118,043 A | 9/2000 | Nies et al. |
| 6,123,731 A | 9/2000 | Boyce et al. |
| 6,132,463 A | 10/2000 | Lee et al. |
| 6,136,029 A | 10/2000 | Johnson et al. |
| 6,136,030 A | 10/2000 | Lin et al. |
| 6,139,578 A | 10/2000 | Lee et al. |
| 6,165,487 A | 12/2000 | Ashkar et al. |
| 6,180,605 B1 | 1/2001 | Chen et al. |
| 6,180,606 B1 | 1/2001 | Chen et al. |
| 6,183,515 B1 | 2/2001 | Barlow et al. |
| 6,187,046 B1 | 2/2001 | Yamamoto et al. |
| 6,187,047 B1 | 2/2001 | Kwan et al. |
| 6,187,329 B1 | 2/2001 | Agrawal et al. |
| 6,203,573 B1 | 3/2001 | Walter et al. |
| 6,203,574 B1 | 3/2001 | Kawamura |
| 6,214,368 B1 | 4/2001 | Lee et al. |
| 6,277,151 B1 | 8/2001 | Lee et al. |
| 6,281,195 B1 | 8/2001 | Rueger et al. |
| 6,287,341 B1 | 9/2001 | Lee et al. |
| 6,300,315 B1 | 10/2001 | Liu |
| 6,306,169 B1 | 10/2001 | Lee et al. |
| 6,309,422 B1 | 10/2001 | Farrington et al. |
| 6,311,690 B1 | 11/2001 | Jefferies |
| 6,326,018 B1 | 12/2001 | Gertzman et al. |
| 6,331,312 B1 | 12/2001 | Lee et al. |
| 6,340,648 B1 | 1/2002 | Imura et al. |
| 6,346,123 B1 | 2/2002 | McKay |
| 6,384,196 B1 | 5/2002 | Weis et al. |
| 6,384,197 B1 | 5/2002 | Weis et al. |
| 6,395,036 B1 | 5/2002 | Czernuszka et al. |
| 6,417,166 B2 | 7/2002 | Liu |
| 6,425,949 B1 | 7/2002 | Lemaitre et al. |
| 6,468,308 B1 | 10/2002 | Kuberasampath et al. |
| 6,479,565 B1 | 11/2002 | Stanley |
| 6,511,510 B1 | 1/2003 | de Bruijn et al. |
| 6,524,345 B1 | 2/2003 | Valimaa et al. |
| 6,540,784 B2 | 4/2003 | Barlow et al. |
| 6,576,015 B2 | 6/2003 | Geistlich et al. |
| 6,764,517 B2 | 7/2004 | Yamamoto et al. |
| 6,846,327 B2 * | 1/2005 | Khandkar et al. ........ 623/16.11 |
| 6,902,584 B2 | 6/2005 | Kwan et al. |
| 6,903,146 B2 | 6/2005 | Matsushima et al. |
| 7,105,182 B2 | 9/2006 | Szymaitis |
| 7,153,938 B2 | 12/2006 | Kikuchi et al. |
| 7,163,965 B2 | 1/2007 | Sotome et al. |
| 7,172,629 B2 | 2/2007 | McKay |
| 7,189,392 B1 | 3/2007 | Kim et al. |
| 7,229,545 B2 | 6/2007 | Sewing et al. |
| 2001/0005797 A1 | 6/2001 | Barlow et al. |
| 2001/0014662 A1 | 8/2001 | Rueger et al. |
| 2001/0014667 A1 | 8/2001 | Chen et al. |
| 2001/0014830 A1 | 8/2001 | Kwan et al. |
| 2001/0014831 A1 | 8/2001 | Scarborough |
| 2001/0016646 A1 | 8/2001 | Rueger et al. |
| 2001/0016772 A1 | 8/2001 | Lee et al. |
| 2001/0018614 A1 | 8/2001 | Bianchi |
| 2001/0031799 A1 | 10/2001 | Shimp |
| 2001/0037014 A1 | 11/2001 | Liu |
| 2001/0041792 A1 | 11/2001 | Donda et al. |
| 2001/0051834 A1 | 12/2001 | Frondoza et al. |
| 2001/0053937 A1 | 12/2001 | Johnson et al. |
| 2002/0013626 A1 | 1/2002 | Geistlich et al. |
| 2002/0018796 A1 | 2/2002 | Wironen |
| 2002/0018797 A1 | 2/2002 | Cui et al. |
| 2002/0018798 A1 | 2/2002 | Sewing et al. |
| 2002/0022883 A1 | 2/2002 | Burg |
| 2002/0022885 A1 | 2/2002 | Ochi |
| 2002/0034532 A1 | 3/2002 | Brodbeck et al. |
| 2002/0042657 A1 | 4/2002 | Pugh et al. |
| 2002/0054901 A1 | 5/2002 | Giainey et al. |
| 2002/0055143 A1 | 5/2002 | Bell et al. |
| 2002/0082594 A1 | 6/2002 | Hata et al. |
| 2002/0082694 A1 | 6/2002 | McKay |
| 2002/0082697 A1 | 6/2002 | Damien |
| 2002/0098222 A1 | 7/2002 | Wironen et al. |
| 2002/0106394 A1 | 8/2002 | Tucker et al. |
| 2002/0128722 A1 | 9/2002 | Jefferies |
| 2003/0152606 A1 | 8/2003 | Gerber |
| 2003/0232071 A1 | 12/2003 | Gower et al. |
| 2004/0131562 A1 | 7/2004 | Gower et al. |
| 2004/0220680 A1 | 11/2004 | Yamamoto et al. |
| 2005/0053638 A1 | 3/2005 | Tanaka et al. |
| 2005/0089579 A1 | 4/2005 | Li et al. |
| 2005/0199156 A1 | 9/2005 | Khairoun et al. |
| 2005/0217538 A1 | 10/2005 | Reinstorf et al. |
| 2006/0093670 A1 | 5/2006 | Mizushima et al. |
| 2006/0204580 A1 | 9/2006 | Gower et al. |

| | | | |
|---|---|---|---|
| 2006/0204581 A1 | 9/2006 | Gower et al. | |
| 2006/0246150 A1 | 11/2006 | Thorne | |
| 2006/0270037 A1 | 11/2006 | Kato et al. | |
| 2006/0292350 A1 | 12/2006 | Kawamura et al. | |
| 2008/0152687 A1* | 6/2008 | Thorne | 424/423 |

FOREIGN PATENT DOCUMENTS

| | | | |
|---|---|---|---|
| EP | 0197693 | A2 | 10/1986 |
| EP | 0243178 | A2 | 10/1987 |
| EP | 0271668 | | 10/1987 |
| EP | 0522569 | | 7/1992 |
| EP | 0747067 | | 5/1996 |
| EP | 0429438 | B1 | 8/1996 |
| EP | 0901795 | | 9/1998 |
| EP | 1127581 | | 2/2000 |
| EP | 1053739 | A1 | 11/2000 |
| EP | 1437148 | A1 | 7/2004 |
| EP | 1500405 | A1 | 1/2005 |
| EP | 1642599 | A1 | 4/2006 |
| JP | 64-076861 | | 3/1989 |
| JP | 01-121059 | | 5/1989 |
| JP | 06-100410 | | 4/1994 |
| JP | 2000-262608 | | 9/2000 |
| WO | 9000892 | A1 | 2/1990 |
| WO | WO9000892 | | 2/1990 |
| WO | 9312736 | A1 | 7/1993 |
| WO | WO9313815 | | 7/1993 |
| WO | WO9415653 | | 1/1994 |
| WO | WO9420064 | | 9/1994 |
| WO | WO9610374 | | 4/1996 |
| WO | WO9610428 | | 4/1996 |
| WO | WO9639203 | | 6/1996 |
| WO | 9639203 | A1 | 12/1996 |
| WO | WO9835653 | | 2/1998 |
| WO | WO9817330 | | 4/1998 |
| WO | WO9851354 | | 5/1998 |
| WO | 9840113 | A1 | 9/1998 |
| WO | WO0045871 | | 2/2000 |
| WO | WO0047114 | | 2/2000 |
| WO | WO00711778 | | 5/2000 |
| WO | WO0045870 | | 8/2000 |
| WO | WO0141821 | | 6/2001 |
| WO | WO0141822 | | 6/2001 |
| WO | WO0174410 | | 10/2001 |
| WO | WO0240963 | | 5/2002 |
| WO | WO0004940 | | 2/2003 |
| WO | 03071991 | A1 | 9/2003 |
| WO | 03092759 | A1 | 11/2003 |
| WO | 2004078120 | A2 | 9/2004 |
| WO | 2004103422 | A1 | 12/2004 |
| WO | 2005051447 | A1 | 6/2005 |
| WO | 2005081699 | A2 | 9/2005 |
| WO | 2005099785 | A1 | 10/2005 |
| WO | 2006031196 | A1 | 3/2006 |
| WO | 2006092718 | A2 | 9/2006 |
| WO | 2007/053850 | A2 | 5/2007 |

OTHER PUBLICATIONS

Noah, E.M. et al., "Impact of Sterilization of the Porous Design and Cell Behavior in Collagen Sponges Prepared for Tissue Engineering", Biomaterials, vol. 23, 2002, pp. 2855-2861.
Alpaslan, C. et al., Bone reaction to subperiosteally implanted hydroxyapatite/collagen/glycosaminoglycans and coral in the guinea pig, Oral Surg. Oral Med. Oral Path., vol. 77, No. 4 (1994), 335-340.
Asahina, I. Repair of Bone Defect in Primate Mandible using a Bone Morphogenetic Protein (BMP)-Hydroxyapatite-Collagen Composite, J. Med. Dent. Sci., vol. 44 (1997), 63-70.
Bar-Shavit, Z. et al., Glucocorticoids Modulate Macrophage Surface Oligosaccharides and Their Bone Binding Activity, J. Clin. Invest., vol. 73 (1984), 1277-1283.
Benque, E. et al., Tomodensitometric and Histologic Evaluation of the Combined Use of a Collagen Membrane and a Hydroxyapatite Spacer for Guided Bone Regeneration: A Clinical Report, Int. J. Oral Maxillofac. Implants, vol. 14 (1999), 258-264.
Borsato, K. et al., Measurement of Partition of Stress Between Mineral and Collagen Phases in Bone Using X-ray Diffraction Techniques, J. Biomechanics, vol. 30, No. 9 (1997), 955-957.
Cornell, C. et al., Multicenter Trial of Collagraft as Bone Graft Substitute, J. Orthop. Trauma, vol. 5, No. 1 (1991), 1-8.
Galbavy, S. et al., Atelocollagen/Hydroxylapatite Composite Material as Bone Defects Fillers in the Experiment on Rats, Bratisl. Med. J., vol. 96 (1995), 368-370.
Grigoryan, A. et al., Time Course of Bone Defect Healing After Implantation in Them of Collagen-Hydroxyapatite Complexes: Experimental and Morphological Study, Stomatologia, vol. 75 (1996), 13-16.
Hamson, K. et al., Preliminary Experience with a Novel Model Assessing In Vivo Mechanical Strength of Bone Grafts and Substitute Materials, Calcif. Tissue Int., vol. 57 (1995), 64-68.
Hsu, F. et al., Microspheres of hydroxyapatite/reconstituted collagen as supports for osteoblast cell growth, Biomaterials, vol. 20 (1999), 1931-1936.
Ito, M., In vitro properties of a chitosan-bonded hydroxyapatite bone-filling paste, Biomaterials, vol. 12 (1991), 41-45.
Katthagen, B. et al., Experimental Animal Investigation of Bone Regeneration with Collagen-Apatite, Arch. Orthop. Trauma Surg. vol. 103 (1984), 291-302.
Kocialkowski, A. et al., Clinical experience with a new artificial bone graft: preliminary results of a prospective study, injury, vol. 21 (1990), 142-144.
Linder, L. et al., Electron Microscopic Analysis of the Bone—Titanium Interface, Acta Orthop. Scand., vol. 54 (1983), 45-52.
Lindholm, T. et al., The role of autogeneic bone marrow in the repair of a skull trephine defect filled with hydroxyapatite granules in the rabbit, Int. J. Oral Maxillofac. Surg., vol. 23 (1004), 306-311.
Mehlisch, D. et al., Histologic evaluation of the bone/graft interface after mandibular augmentation with hydroxylapatite/purified fibrillar collagen composite implants, Oral Surg. Oral Med. Oral Pathol., vol. 70 (1990), 685-692.
Minabe, M. et al., Histological Study fo the Hydroxyapatite-Collagen Complex Implants in Periodontal Osseous Defects in Dogs, J. Periodontol., (Oct. 1988), 671-678.
Mittelmeier, H. et al., Clinical Experience in the Implantation of Collagen-Apatite for Local Bone Regeneration, Z. Orthop., vol. 121 (1983), 115-123.
Pasquier, G. et al., Injectable percutaneous bone biomaterials: an experimental study in a rabbit model, J. Mat. Sci. Mat. Med., vol. 7, No. 11 (1996), 683-690.
Pohunkova, H. et al., Reactivity and the fate of some composite bioimplants based on collagen in connective tissue, Biomaterials, vol. 16 (1995), 67-71.
Rovira, A. et al., Colonization of a calcium phosphate/elastin-solubilized peptide-collagen composite material by human osteoblasts, Biomaterials, vol. 17 (1996), 1535-1540.
St. John, K. et al., Response of Canine Bone to a Synthetic Bone Graft Material, Clin. Mat., vol. 12 (1993), 49-55.
Suganuma, J. et al., In vivo Evaluation of Collagen-Coated Dacron Fiber in Bone, Clin. Mat., vol. 15 (1994), 43-50.
Zerwekh, J. et al., Fibrillar Collagen-Biphasic Calcium Phosphate Composite as a Bone Graft Substitute for Spinal Fusion, J. Orthop. Res., vol. 10 (1992), 562-572.
Cornell, C., Initial clinical experience with use of Collagraft as a bone graft substitute, Techniques Orthop., vol. 7, No. 2 (1992), 55-63.
International Search Report, mailed Mar. 7, 2008.

* cited by examiner and molded in site into desired shapes. These products are desirable for the reconstruction of skeletal defects, e.g., in spine, dental, and/or other orthopedic surgeries. They may be used as a substitute for autologous bone grafts or may be used in conjunction with autologous bone grafts.

BONE GROWTH PARTICLES AND OSTEOINDUCTIVE COMPOSITION THEREOF

FIELD OF THE INVENTION

The invention relates generally to a composition comprising bone growth particles, a method of making the composition, and a use of the composition in promoting bone growth.

BACKGROUND

The use of osteoinductive proteins or growth factors, such as bone morphogenetic proteins (BMPs), mitogenic growth factors, etc., improves clinical outcomes after surgical reconstruction of skeletal defects (e.g., implants). Such osteoinductive factors induce bone formation by targeting and activating undifferentiated perivascular connective tissue cells. Mitogenic growth factors target and accelerate the osteogenic activity of previously differentiated cells. Although advances have improved the biological activity of osteoinductive factors, their clinical application has been limited by the requirement for a superior tissue scaffold/delivery vehicle.

Autologous bone grafts are the gold standard for restoring skeletal defects because they provide both a natural tissue scaffold and osteoinductive growth factors. Allogenic grafts may also be used, such as demineralized bone matrices. For example, demineralized bone material can be prepared by grinding a bone, demineralizing it with an acid solution, washing with a phosphate buffered solution, washing with ethanol and drying it. Demineralized bone material can also be obtained from a commercial bone or tissue bank (e.g., AlloSource, Denver Colo.). Because autogenic and allogenic sources of human bone are limited and may be expensive or painful to obtain, the use of substitute materials is preferred. Numerous synthetic or modified natural materials have been experimentally evaluated as alternative delivery vehicles, and include but are not limited to products containing hydroxyapatites, tricalcium phosphates, aliphatic polyesters (poly(lactic) acids (PLA), poly(glycolic)acids (PGA), polycaprolactone (PCL), cancellous bone allografts, human fibrin, plaster of Paris, apatite, wollastonite (calcium silicate), glass, ceramics, titanium, devitalized bone matrix, non-collageneous proteins, collagen and autolyzed antigen extracted allogenic bone. However, these synthetic or modified natural materials have yet to result in delivery vehicles having osteoinductivity comparable to autograft or allograft bone sources, or having the capability to enhance the osteoinductivity of these or other osteoinductive materials.

Alternate products are desirable.

SUMMARY OF THE INVENTION

Biocompatible compositions that comprise bone growth particles, a method of making the compositions, and uses of the compositions in promoting bone growth are disclosed. One embodiment is a bone growth-promoting composition comprising collagen and calcium phosphate that can be formulated as a paste or putty. The compositions and methods facilitate skeletal regeneration and provide a scaffold for new bone growth.

The compositions may be formulated as pastes or putties. This provides ease of use and economy of product manufacture. Pastes and putties are soft masses with physical consistencies between a liquid and a solid. Pastes and putties are desirable for surgical bone repair as they can be more easily delivered to difficult surgical sites and molded in site into desired shapes. These products are desirable for the reconstruction of skeletal defects, e.g., in spine, dental, and/or other orthopedic surgeries. They may be used as a substitute for autologous bone grafts or may be used in conjunction with autologous bone grafts.

In one embodiment, engineered (i.e., synthetic) composite products that enhance the in vivo formation of bone tissue and preserves the availability, and thus the functional activity of osteoinductive growth factors are disclosed. Local pH control enhances clinical efficacy of osteogenic proteins, and supplements local availability of essential bone components such as collagen, calcium, and phosphate. Moderately acidic microenvironments likely improve protein-stimulated osteoinduction by enhancing the rates of protein solubilization and protein release from collagen. Supplementing the local concentration of soluble $[Ca^{2+}]$ and $[PO_4^{3-}]$ ions enhances the quantity of bone produced, and increases rate of bone formation by reducing dependence on essential ion diffusion from serum and other body fluids. The resultant increase in local concentration and cellular availability of bone morphogenetic proteins result in improved acidic collagen delivery vehicles.

One embodiment is a biocompatible synthetic bone growth composition comprising a particulate composite of a fibrillar collagen component and a calcium phosphate component. The collagen component may be insoluble collagen (e.g., crosslinked collagen or porous particles). The calcium phosphate component may be acidic calcium phosphate, such as monocalcium phosphate $[Ca(H_2PO_4)_2]$, calcium hydrogen phosphate dihydrate $[CaHPO_4\ 2H_2O]$, anhydrous calcium hydrogen phosphate $[CaHPO_4]$, partially dehydrated calcium hydrogen phosphate $[CaHPO_4 xH_2O$, where x is between and includes 0 and 2] and/or calcium pyrophosphate $[2CaO.P_2O_5]$. In one embodiment, the composition contains an osteoinductive component, e.g., a purified bone growth factor, a recombinant bone growth factor, a bone marrow component, a blood component, demineralized bone, autologous bone, bone marrow aspirate, etc. In one embodiment, the composition pH ranges from about pH 5 to about pH 7.

Another embodiment is a process for producing a bone growth composition. A collagen component is combined with a calcium phosphate component to produce a mineralized collagen component. The mineralized collagen component may be prepared as a collagen gel, which may be frozen and lyophilized into a product referred to as a sponge. Particles of the mineralized collagen component (e.g. sponge) may be prepared by grinding, milling, chopping and/or molding the mineralized collagen component. The particulate composition may be packaged as a kit that may include a device (e.g., container) for mixing the particles with a fluid. An osteoinductive component may be added, either before or after forming the particles.

Another embodiment is a method of facilitating bone growth in a patient by adding an osteoinductive component to a particulate mineralized collagen component and implanting the composition in the patient. The composition may be injected into and/or molded to fit a surgical site.

These and other embodiments will be further appreciated with respect to the following drawings, description, and examples.

DETAILED DESCRIPTION

Figures 1, 2:
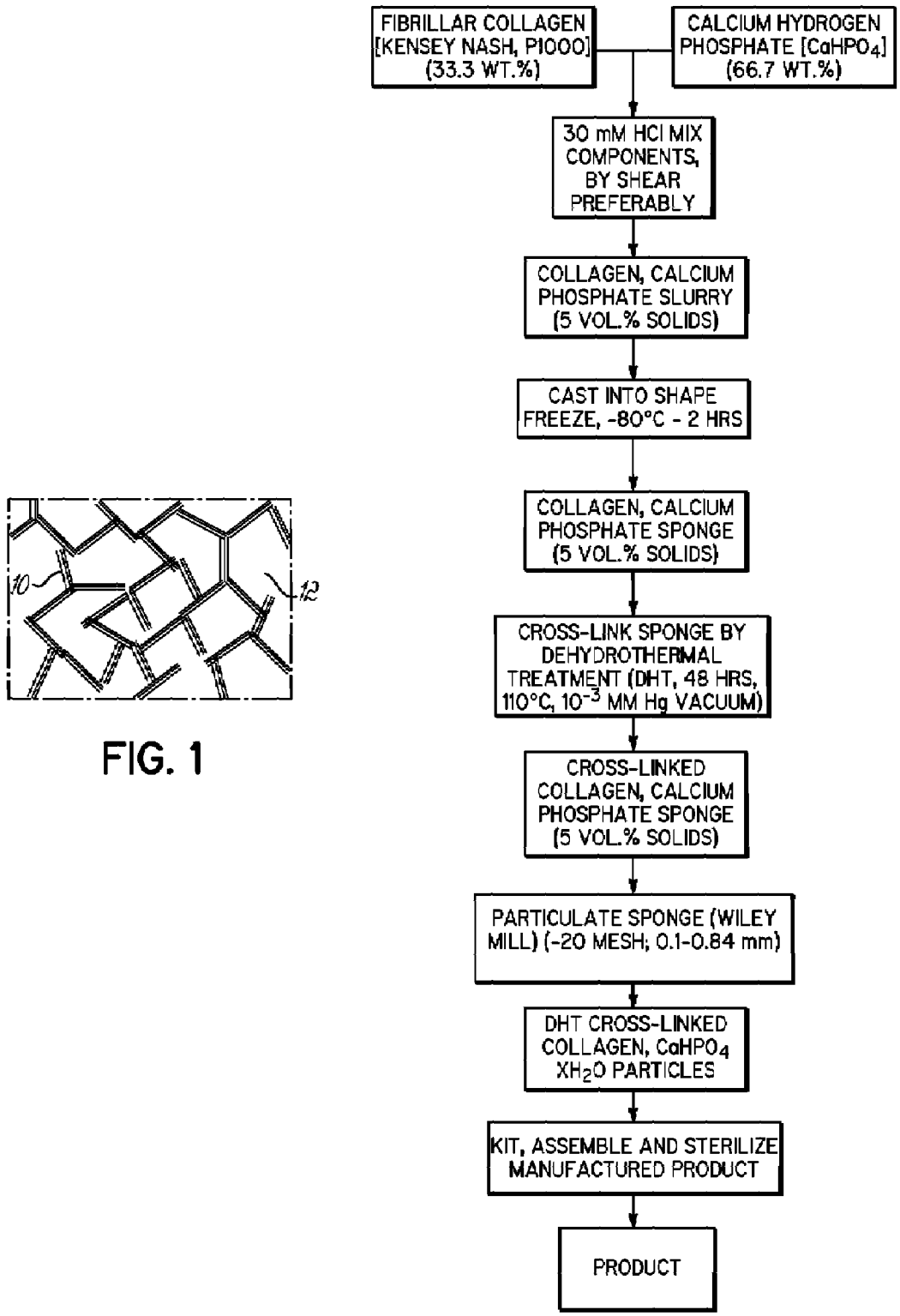
FIG. 1 shows a schematic representation of a collagen scaffold.
FIG. 2 shows a flow chart representing a process for making a mineralized collagen component.

The basic elements required for bone formation include a three-dimensional, open-porosity tissue scaffold, cells, and osteoinductive signaling molecules to stimulate cell differentiation, proliferation and matrix formation. Successful bone formation requires that these elements be combined in a well-coordinated spatial and time dependent fashion. The relative contribution of each element may vary, e.g., according to differences in patient age, gender, health, systemic conditions, habits, anatomical location, etc.

Embodiments for improved bone formation and healing include the following: biocompatible, open-porous bone tissues scaffold, enhanced local concentration of soluble bone mineral elements such as calcium and phosphate, and preserved osteoinductive protein solubility. Each is subsequently analyzed.

A biocompatible, open-porous bone tissue scaffold restores function and/or regenerates bone by providing a temporary matrix for cell proliferation and extracellular matrix deposition with consequent bone in-growth until new bony tissue is restored and/or regenerated. The matrix may also provide a template for vascularization of this tissue. The scaffold may actively participate in the regenerative process through the release of growth differentiation factors.

The macro and micro-structural properties of the scaffold influence the survival, signaling, growth, propagation, and reorganization of cells. They may also influence cellular gene expression and phenotype preservation. The following properties contribute to scaffold characteristics for bone formation: cell biocompatiability, surface chemistry, biodegradability, porosity, and pore size.

In one embodiment, the composition comprises fibrillar collagen. Collagen is the main protein of connective tissue in animals and the most abundant protein in mammals. Bone is composed of strong, fibrillar bundles of collagen encased within a hard matrix of a calcium phosphate known as hydroxylapatite. Collagen is also a constituent in cartilage, tendon and other connective tissues.

The collagen protein possesses a distinctive triple-helix tertiary structure of three polypeptide chains supercoiled about a common axis and linked by hydrogen bonds. At least nineteen distinct molecules have been classified as collagens, and specific types are associated with particular tissues. Collagen can be converted into gelatin by boiling or treating with an acid. The solubility of collagen is affected by its conformation and extent of associations, whereby newly synthesized collagen chains are generally soluble but after formation of fibrils, they become essentially insoluble.

Collagen fibrils, referred to as fibrillar collagen, result from covalent cross-linking between the supercoiled chains by an enzymatic mechanism that strengthens and stabilizes the chains. Fibrillar collagen may be obtained from native sources such as human or animal dermis, tendon, cartilage or bone. It is generally recovered by proteolytically degrading natural collagen crosslinks to produce tropocollagen. Tropocollagen, the basic amino acid component, is soluble with acidic solutions (in one embodiment, between pH 3 to pH 4). These solutions can be cleaned and purified prior to collagen fiber reassembly by pH neutralization. Fibrillar collagen is generally less dense, less soluble, and swells more in solution than non-fibrillar collagen.

Due to its high degree of biocompatibility with the human body, collagen has been successfully used in a variety of medical and dental applications for many years with minimal adverse responses. During its manufacture, potentially antigenic portions of the collagen molecule are removed, resulting in a product that is highly biocompatible and well-tolerated by the tissue. Collagen is also chemotactic for fibroblasts and other cells involved in bone tissue repair. Collagen biocompatibility ensures that the products are well integrated in the host tissue without eliciting an immune response.

Collagen used in the particulate composition may be from any source. These include natural sources such as human and mammalian tissues, and synthetic sources manufactured using recombinant technologies. It may be of any type (e.g., collagen Types I, II, III, X and/or gelatin). In one embodiment, collagen used is Type I collagen. In one embodiment, collagen is derived from bovine dermis. In one embodiment, fibrillar collagen is derived from bovine dermis manufactured by Kensey Nash Corporation (Exton Pa.) under the name Semed F. In one embodiment, fibrillar collagen may be obtained from Kensey Nash Corporation under the name P1000. In one embodiment, the particles comprise at least about 33 percent by dry weight collagen. In another embodiment, the particles comprise from about 25 percent to about 75 percent dry weight collagen.

The surface chemistry of the scaffold can control and affect cellular adhesion. It can also influence the solubility and availability of proteins essential for intracellular signaling. Intracellular signaling maximizes osteoinductivity through controlled cellular differentiation, proliferation, and stimulation.

Collagen fabricates the disclosed structural scaffold and provides a physical and chemical milieu favorable to bone regeneration. Collagen also provides a favorable extracellular matrix for bone forming cells, e.g., osteoblasts, osteoclasts, osteocytes, etc. The bone forming cells' natural affinity for the collagen matrix has been demonstrated to favorably influence the function and signaling required for normal cellular activity.

The degradation rate of the scaffold should ideally match the bone-healing rate. Slower degradation rates can hinder the rate of remodeled, load-bearing bone formation. Faster degradation can result in unhealed defects.

The solubility and resorption of collagen is affected by its conformation and the degree of collagen cross-linking. The in vivo solubility and resorption of collagen is also influenced by the local concentration of proteolytic agents and vascularity at the site.

In one embodiment, the composition is crosslinked to control the solubility and the extent and rate of collagen resorption. Collagen crosslinking may occur by various methods such as dehydrothermal (DHT), UV light exposure, chemical crosslinking with aldehydes (i.e. glyceraldehyde, formaldehyde, glutaraldehyde), carbodiimides and various amino acids. The crosslinking conditions will preserve the in vivo lifetime of the composition for up to about twelve weeks, allowing it to function as a scaffold for bone healing. Collagen is eventually absorbed into the surrounding tissue by host enzymes. In one embodiment, uncrosslinked collagen may be a component of the composition.

Scaffolds desirably posses an open pore, fully interconnected geometry to allow homogeneous and rapid cell in-growth, and facilitate vascularization of the construct from the surrounding tissue.

To this end, the total pore volume porosity of the scaffold simulates that of cancellous bone. Cancellous bone is a highly porous structure (about 50 vol. % to about 90 vol. %) arranged in a sponge-like form, with a honeycomb of branching bars, plates, and rods of various sizes called trabeculae. The synthetic scaffold must ensure pore interconnectivity to allow for the diffusion of nutrients and gases and for the removal of metabolic waste resulting from the activity of the cells within the scaffold. It is generally accepted by one skilled in the art that the pore diameters should be within the range of about 200 µm to about 900 µm range for ideal bone formation. Smaller pores can occlude and restrict cellular penetration, matrix production, and tissue vascularization. Larger pores can detrimentally influence the mechanical properties of the structural scaffold.

(dical), an example of a calcium phosphate additive used in the disclosed composition, provides about 200 to about 300 times the concentration of soluble mineral elements in comparison to conventional calcium phosphates, such as tricalcium phosphate (TCP) ($Ca_3(PO_4)_2$) or tetracalcium phosphate (TTCP) ($Ca_4(PO_4)_2(OH)_2$) or calcium hydroxyapatite (HA) ($Ca_5(PO_4)_3(OH)$).

TABLE 1

Equilibrium solubility of calcium and phosphate ions from several different biologically compatible calcium phosphate salts.

|  | Equilibrium [$Ca^{2+}$] | Equilibrium [$PO_4^{3-}$] | Insoluble fraction [200 mg/cc] |
|---|---|---|---|
| Plasma | 2,200.0 µM | 1,100.0 µM | — |
| $Ca(H_2PO_4)_2$ (Monocal) | 14,300.0 µM | 28,600.0 µM | 97.0000 wt. % |
| $CaHPO_4$ (Dical) | 480.0 µM | 480.0 µM | 99.9700 wt. % |
| $Ca_3(PO_4)_2$ (TCP) | 1.4 µM | 0.9 µM | 99.9999 wt. % |
| $Ca_5(PO_4)_3(OH)$ (HA) | 2.2 µM | 1.3 µM | 99.9999 wt. % |
| $Ca_4(PO_4)_2(OH)_2$ (TTCP) | 28.2 µM | 14.1 µM | 99.9994 wt. % |

The disclosed method produces a synthetic scaffold that mimics the natural structural design of bone for bone formation. In one embodiment, the scaffold is fabricated using fibrillar collagen. Fibrillar collagen is the cytoskeletal filament within the matrix of all tissues and organs. In addition to being a fundamental element of natural bone, fibrillar collagen allows the formation of a scaffold with high surface area and an interconnected network of high porosity, as shown in FIG. 1. The total pore volume is made up of both micropores 10, which is the space between collagen strands within the fibril and macropores 12, which is the space between collagen fibrils. In one embodiment, the composition matches the porosity of cancellous bone, with total pore volumes ranging between about 50 vol. % to about 97 vol. % and pore diameters ranging between 1 µm and 1000 µm.

Enhancing local concentration of soluble bone mineral elements, such as [$Ca^{2+}$] and/or [$PO_4^{3-}$], contributes to improved bone formation and healing.

Calcium phosphate based products have been used for bone repair for over 80 years. Their many desirable properties include similarity in composition to bone mineral, bioactivity (ability to form apatitic or carbonated hydroxylapatite on their surfaces), ability to promote cellular function and expression, ability to form a direct strong interface with bone, and osteoconductivity (ability to provide a scaffold or template for the formation of new bone). Commercially available calcium phosphate biomaterials differ in origin (e.g., natural or synthetic), composition (e.g., hydroxylapatite, beta-tricalcium phosphate, and biphasic calcium phosphate), physical forms (e.g., particulates, blocks, cements, coatings on metal implants, composites with polymers), and physicochemical properties. Subtle differences in chemical composition and crystalline structure may significantly impact their in vivo physical and biological performance.

The disclosed composition and method supplements the local availability of essential soluble bone components, e.g., calcium and phosphate. Biologically compatible, sparingly soluble calcium phosphates are suitable supplements to locally increase the supply of soluble calcium [$Ca^{2+}$] and phosphate [$PO_4^{3-}$] ions. As shown in Table 1, calcium phosphate salts solubilize at different equilibrium ionic concentrations, where the local supplemented concentrations of calcium [$Ca^{2+}$] and phosphate [$PO_4^{3-}$] ions can vary by more than four orders of magnitude. Calcium hydrogen phosphate Dical is soluble and does not require osteoclastic resorption for biodegradation. It resorbs slowly enough that products can be designed to supplement the soluble mineral ion concentration for several weeks.

Local supplementation of soluble [$Ca^{2+}$] and [$PO_4^{3-}$] ions enhanced the quantity of bone produced and increased its rate of formation in animals. Without being bound by a specific theory, it is believed that the use of a soluble form a calcium phosphate reduces the healing rate dependence on local osteoclastic resorption and essential ion diffusion from plasma fluids.

The method and composition preserved osteoinductive protein solubility. Osteoinduction is the process by which stem cells and osteoprogenitor cells are recruited to a bone-healing site and are stimulated to undergo the osteogenic differentiation pathway. Classic synthetic, biodegradable scaffolds are only osteoconductive and require combination with an inductive bone-forming agent to stimulate and accelerate bone healing.

Bone growth factor cytokines, also known as bone morphogenetic proteins (BMPs), are entrapped at high concentration within bone and are secreted by many bone-forming cell types. The primary function of BMPs is cellular signaling. Intracellular signaling occurs through the binding of a soluble growth factor to a specific cell receptor site. This signal pathway stimulates several different and important bone healing events, including the proliferation, migration, and differentiation of bone forming cells. The cells are, in turn, responsible for the synthesis of other proteins and growth factors that are important for regulating and controlling bone tissue formation. Although there is a vast array of BMPs described and known to one skilled in the art, BMPs 2, 4, 6 and 7 are generally considered to be the most osteoinductive.

The disclosed composition provides biodegradable synthetic bone graft materials to specifically preserve the solubility of osteoinductive proteins. Various forms of calcium phosphates are known to have different chemical affinities for endogenous osteoinductive proteins (e.g., BMPs). Calcium phosphates such as TCP and HA are known to strongly bind acid-soluble BMPs because of their alkaline surface chemistry. In contrast, dical presents a moderately acidic surface chemistry that will not bind acidic proteins. Because of its enhanced solubility, it can also moderately buffer the local environment to an acidic range that further preserves osteoinductive BMP solubility.

An in vitro study assessed the influence of variable composition calcium phosphate salts on the soluble concentration of osteoinductive proteins. The residual concentration of soluble recombinant BMP-2 was measured after exposing a controlled concentration aliquot to an equi-molar quantity of calcium phosphate salt. As shown in Table 2, moderately acidic calcium phosphates salts, such as dical, preserved the highest soluble concentration of osteoinductive proteins. The enhanced local concentration and cellular availability of bone morphogenetic proteins (BMPs) better stimulate bone formation.

TABLE 2

Equilibrium solubility of osteoinductive recombinant human BMP-2 protein in the presence of equimolar concentrations of various calcium phosphates.

| | [rhBMP-2] mg/ml | [rhBMP-2] % |
|---|---|---|
| Control | 15.0 | 100% |
| $Ca(H_2PO_4)_2$ (monocal) | 15.0 | 100% |
| $CaHPO_4$ (dical) | 11.4 | 76% |
| $Ca_3(PO_4)_2$ (TCP) | 3.5 | 23% |
| $Ca_5(PO_4)_3(OH)$ (HA) | 2.3 | 15% |

In one embodiment, an additive (e.g., an osteoinductive component) formulated as a putty or paste is included in the biocompatible composition that facilitates skeletal regeneration and provides a scaffold for new bone growth. Use of synthetic components reduces the potential of disease transfer and immune system incompatibilities. The terms putty and paste are qualitative and generally describe a composition that is moldable/formable and flowable, respectively. When the term paste is used to describe the composition including a liquid, it is to be understood that a putty may also be formed, generally by decreasing the volume of liquid mixed with the composition.

In one embodiment, the composition forms a paste that enhances the formation of bone tissue and increases the availability, and thus the functional activity of osteoinductive growth factors. It is provided at a surgical site during reconstruction of a skeletal defect. For example, the paste may be used in spine, dental, reconstructive, trauma, and other orthopedic surgeries. The paste may be used as a substitute for or additive to autologous bone grafts. Although the composition is synthetic, it may include natural components, e.g., bovine collagen, and/or be combined with natural components, e.g., bone marrow aspirate.

The paste controls pH to enhance clinical efficacy of osteoinductive proteins, and supplements local availability of bone components such as collagen, calcium, and phosphate. Without being bound by a specific theory and as analyzed above, moderately acidic microenvironments likely improve protein-stimulated osteoinduction by enhancing the degree of protein solubilization and protein release from collagen. Supplementing the local concentration of soluble $[Ca^{2+}]$ and $[PO_4^{3-}]$ ions increases the rate of bone formation by reducing dependence on ion diffusion from serum and other body fluids. The resultant increase in local concentration of collagen and mineral building blocks, coupled with the enhanced cellular availability of bone morphogenetic proteins, improves acidic collagen delivery vehicles.

In one embodiment, the composition formulated as a paste is both osteoinductive, i.e., it initiates or induces bone growth, and osteoconductive, i.e., it facilitates already initiated bone growth but does not itself initiate bone growth. Its osteoinductive effect arises, for example, from osteoinductive factors present in the liquid, e.g., bone marrow aspirate, used to make the paste. The composition is also osteoinductive in that it does not inhibit or diminish the solubility of osteoinductive factors, such as BMPs, due to the ability of the composition to induce a local pH decrease, as analyzed above. Its osteoconductive effect arises from provision of a collagen scaffold and source of bone growth materials. In one embodiment, exogenous osteoinductive factors are included as additives in the composition.

A variety of calcium phosphate salts, represented by the general chemical formula $xCaO,P_2O_5$, may be used to simultaneously supplement the local $[Ca^{2+}]$ and $[PO_4^{3-}]$ ion concentrations and to act as short-term biologic buffers. In one embodiment, the composition includes a particulate formed from crosslinked collagen and calcium phosphate.

In another embodiment, a method of making the particulate composition is provided. Collagen and calcium phosphate are combined, dried, crosslinked, and particulated as subsequently described.

In another embodiment, a method of using the collagen and calcium phosphate particles is disclosed. The particulate composition can be combined with a fluid, for example bone marrow aspirate, to create a paste. The paste is then injected, manually applied, or otherwise delivered to a site of a bone. In one embodiment, the paste is an injectible bone void filler. The paste provides improved handling and delivery capabilities, allowing a surgeon to introduce the composition into complex geometry bone defects. The paste components are fully resorbable and stimulate bone regeneration in a manner similar to that achieved with natural bone.

In one embodiment, the composition contains particulate, fibrillar collagen and calcium phosphate. The composition can be combined with a liquid such as biological fluids (e.g., bone marrow aspirate, whole blood, serum, plasma, etc.) to form a paste. The paste is then used as an injectable and/or conformable (i.e., moldable) bone-grafting material for primary applications in, e.g., spine fusion, dental furcation augmentation, fracture repair, etc.

In one embodiment, where a fibrillar collagen component is combined with a calcium phosphate component to produce a mineralized collagen component, porous particles of the mineralized collagen component may be prepared. In one embodiment, particle porosity measured as the total open pore volume is greater than about 90 percent by volume. In another embodiment, the total open pore volume within the particle ranges from about 50 percent to about 97 percent. In one embodiment, particle pore size ranges from about 1 µm to about 1000 µm. In another embodiment, particle pore sizes range from about 125 µm to about 300 µm. In one embodiment, the particle size ranges from about 100 µm to about 840 µm.

A variety of calcium phosphate salts, represented by the general chemical formula $Ca_x(PO_4)_y(O,OH,H_2O)$ may be used in the product composition to simultaneously supplement the local concentration of $[Ca^{2+}]$ and $[PO_4^{3-}]$ ion concentrations and to act as short-term biologic buffers. Calcium phosphates that may be used in the composition include monocalcium phosphate (monocal) $[Ca(H_2PO_4)_2]$, calcium hydrogen phosphate (dical) $[CaHPO_4]$, calcium pyrophosphate $[2CaO.P_2O_5]$, tricalcium phosphate $[3CaO.P_2O_5]$, hydroxyapatite $[3.33CaO.P_2O_5(OH)_2$ (polycrystalline and amorphous compositions)], tetracalcium phosphate $[4CaO.P_2O_5]$ and calcium carbonate $[CaCO_3$ (aragonite), $CaCO_3$ (calcite)]. In one embodiment, the composition comprises an acidic mixture of calcium phosphates. Acidic calcium phosphate refers to those compositions, with composite calcium (x)/phosphate (y) below 1.5, that either present acidic surface chemistries or solubilize in aqueous solution to a sufficient extent to cause solution buffering to an acidic value (pH<7.0). In one embodiment, the acidic calcium phosphate is calcium hydrogen phosphate dihydrate [$CaHPO_4.2H_2O$]. In one embodiment, the acidic calcium phosphate is anhydrous calcium hydrogen phosphate [$CaHPO_4$]. In one embodiment, the calcium phosphate of the composition is greater than about 25 percent by dry weight. In another embodiment, the calcium phosphate of the particulate composition is about 67 percent by dry weight.

The composition may further comprise additives such as bioactive agents, e.g., agents that exhibit biologic activity, and liquids. For example, agents that are osteoinductive and/or osteogenic may be included. As previously stated, osteoinductive agents stimulate bone growth. Examples of osteoinductive agents include bone growth factors, bone marrow components, blood components, and bone components. Bone growth factors may be purified or recombinant and include bone morphogenetic protein (BMP). Bone marrow aspirates (BMA) may be used in the composition because they contain osteoinductive agents such as bone growth factors and mesenchymal stem cells. Mesenchymal stem cells (MSCs) are multi-potent cells capable of differentiating along several lineage pathways to aid in the production of bone. MSCs are considered as a readily available source of cells for many tissue engineering and regenerative medicine applications. For these reasons, osteoinductive proteins and MSCs have been used to supplement the performance of osteoconductive bone formation scaffolds as replacements for autologous and allogeneic bone grafts.

In one embodiment, bone marrow aspirate is included in the composition. Blood components such as whole blood and platelet-rich plasma, may be included in the composition. Osteoinductive bone components that may be included in the composition include demineralized bone and autologous bone. Demineralized bone refers to bone that has been treated to remove all or a majority of the calcium phosphate mineral components. Demineralization is usually performed by exposing powdered bone, from any human or mammalian source, to acidic solutions (i.e., HCl, acetic acid, ethylene diamine tetracetic acid) with a pH less than about 4. Bone that has not been demineralized may be included in the composition and also includes bone derived from an autologous or mammalian source.

Adding liquid to the composition results in a paste or putty, defined as soft masses with physical consistencies between a liquid and a solid. The liquid may be a biological fluid such as blood, plasma, serum, bone marrow, etc., or may be a buffer or may be capable of buffering to the physiological pH values of human serum (pH 7.1 to pH 7.4). Examples of buffers are known to one skilled in the art and include Tris and phosphate-buffered saline. In one embodiment, the composition has a pH in the range of about pH 5 to about pH 7.4. In another embodiment, the composition has a pH in the range of about pH 5.5 to about pH 6.9. More than one liquid may be included in the composition. For example, the composition may include bone marrow aspirate and a buffering salt solution. The liquid may also include biocompatible liquids such as water, saline, glycerin, surfactants, carboxylic acids, dimethylsulfoxide, and/or tetrahydrofuran. In one embodiment, the liquid is greater than about 25 percent by volume of the composition. In another embodiment, the liquid comprises from about 75 percent to about 90 percent by volume of the composition. Additionally, natural and synthetic polymers such aliphatic polyesters, polyethylene glycols, polyanhydrides, dextran polymers, and/or polymeric orthophosphates may be included in the composition.

In one embodiment, a process for producing a particulate mineralized collagen composition comprising collagen and calcium phosphate is provided. In one embodiment, a crosslinked collagen and calcium phosphate composition is prepared and is then formed into particles, as shown in FIG. 2. Initially, collagen and calcium phosphate are combined with an acid, e.g. HCl, to create a slurry. The slurry may also be a gel due to the presence of collagen in an acidic environment. The types of collagen that may be used are described above and include bovine dermal fibrillar collagen. Suitable calcium phosphate includes acidic calcium phosphate such as monocalcium phosphate [$Ca(H_2PO_4)_2$], calcium hydrogen phosphate [$CaHPO_4$], and/or calcium pyrophosphate [$2CaO.P_2O_5$]. In one embodiment, about 33 percent by weight of collagen is combined with about 67 percent by weight calcium phosphate.

The combination is then subjected to freezing, lyophilization, and crosslinking. In one embodiment, the composition is frozen at about −80° C. for about two hours. In one embodiment, the composition is lyophilized for at least about sixteen hours. In another embodiment, the composition is lyophilized for at least about 48 hours.

The composition may be crosslinked. Crosslinking may be effected by a variety of methods known to one skilled in the art, including but not limited to dehydrothermal (DHT) crosslinking. In DHT crosslinking, the composition is placed in a vacuum oven chamber, the chamber is evacuated to create a vacuum, and the composition is heated for a period of time. In one embodiment, the composition is heated to about 110° C. In one embodiment, the composition is heated in a vacuum oven for about 48 hours.

Following freezing, lyophilization, and crosslinking, the solid composition is formed into particles. Methods of forming particles are known to one skilled in the art and include, but are not limited to, grinding, milling, chopping, and/or molding. In one embodiment, particles are formed by milling the solid composition. Milling may occur using a Wiley mill (Thomas Scientific, Swedesboro N.J.). The mesh size on the mill directs the size of the resultant particles. In one embodiment, a −20 mesh is used that creates particles in the range of about 100 µm to about 840 µm. The particles may be sized by, for example, sieving. At any point in the process, additional components may be added to the composition, as described above. For example, an osteoinductive component can be added prior to forming the articles.

The composition may be provided as a kit. In one embodiment, the kit includes the composition described above, and may further include other components. These include a receptacle such as a plastic container in which to place the composition and in which to add liquid to form the composition into a paste or putty, a mixing implement such as a spatula, stir rod, etc., a disposable syringe barrel without a needle in which to place and deliver the mixed paste, instructions for formulating and/or using the composition, etc.

In another embodiment, a method of facilitating bone growth is provided. In one embodiment, the method includes adding at least one osteoinductive component such as a purified bone growth factor, a recombinant bone growth factor, a bone marrow component, a blood component, demineralized bone, autologous bone, etc., to the particulate composition previously described. In embodiments where the osteoinductive component is bone marrow aspirate, blood, or a blood component, it may be acutely obtained and added to the composition (e.g., blood and/or bone marrow may be obtained from the same surgical site for repairing the defect). Adding the osteoinductive component(s) and/or another liquid to the composition, with stirring, results in a paste or putty, which is provided to the desired anatomical site of the patient. In one embodiment, the paste is loaded into the barrel of a disposable 5 cc syringe, without a needle attached, and is extruded through the barrel aperture to the desired anatomical site. In another embodiment, the putty is manipulated or formed into a configuration of desired size, shape, length, etc., either manually or by instrumentation, and gently pressed on and/or in the desired anatomical site. The site is desirably prepared to expose healthy bleeding bone, facilitating subsequent bone growth. The method may be performed using minimally invasive procedures known to one skilled in the art. The method may be used in at least partially filling bone voids and/or gaps of the skeletal system (i.e., extremities, pelvis, spine, oral cavity) that are not intrinsic to the stability of the bone structure. These voids and/or gaps may be a result of trauma, either natural or by surgical creation. The paste is gently provided on and/or in the void and/or gap. The paste is resorbed by the body during the healing process (over days, weeks, and months). The paste may be molded into the bone void or defect by manipulating either manually or using an instrument (e.g., spatula, syringe, probe, cannula, etc.).

The following examples further illustrate embodiments of the invention.

EXAMPLE 1

A composite collagen and calcium phosphate gel dispersion was prepared (5 vol. % collagen gel) by weighing 6 g collagen. A 10 mM HCl solution was volumetrically measured (246 ml) to prepare a 5 vol. % gel. Twelve g sterilized dicalcium phosphate [$CaHPO_4$] powder (66.7 wt. % calcium phosphate) was added and stirred to a uniform consistency. The combination was mixed, for example, by repeated shear material transport, until a uniform collagen gel dispersion of moderate viscosity (about 1,000 P to about 1,500 P) was obtained.

About 16.5 ml of the collagen and calcium phosphate gel dispersion was then cast into an autoclaved TEFLON® mold of 4.5 cm (L)×1.7 cm (W)×2.1 cm (H), with removable upper and lower autoclaved glass plates. The collagen gel dispersion was injected into the mold with the lower glass plate attached and the composition was evenly spread using a spatula. The upper autoclaved glass plate was then fixed in contact with the dispersion and the plates were secured using countersunk flat head screws. The mold was then maintained at −80° C. for at least one hour.

After freezing, the glass plates were removed from both sides of the mold backing and the mold containing the frozen product was placed in a sterile paper autoclave pouch and frozen within a glass lyophilization vessel for two hours.

The frozen composition was then lyophilized (i.e. freeze-dried) at room temperature in a Laboratory Freeze Dryer (Freezemobile 25EL, VirTis Inc., Gardiner N.Y.) for at least 24 hours. The lyophilization vessel containing the product was attached to the vacuum port of the Freezemobile in operation with a condenser temperature of −50° C. or below, and a manifold pressure of $10^{-3}$ mm Hg or less. The vacuum port to the vessel was opened exposing the frozen product to pressure sufficient to freeze dry the product within 24 hours at room temperature.

The composition was then crosslinked via a dehydrothermal (DHT) process. The composition was removed from the mold and placed onto an autoclaved aluminum pan. The samples were then placed into a vacuum oven. The gas vents were closed and the chamber was evacuated to $10^{-3}$ mm Hg. The vacuum chamber was heated to 110° C. After 48 hours of constant temperature heating, the samples were cooled to room temperature (about 20° C. to about 22° C.) under vacuum. After the composition bar cooled, the chamber was repressurized with 0.2 micron filtered air. The composition bar was removed using sterile forceps and stored in a sterile paper autoclave pouch.

The samples were then processed into particles. Samples were placed into the hopper of a clean Wiley Mini-Mill (Thomas Scientific, Swedesboro N.J.), and milled at about 1,700 rpm. The samples were swept around by rotor until cut to sufficient fineness to pass through the sieve top of a delivery tube that formed the bottom of the chamber. The final product was collected using a 20 mesh delivery unit located under the mill blades.

In one embodiment, the particles were also subjected to compression molding to form storage disks. The particles were weighed and introduced into a cylindrical mold to produce solid disks through uni-axial compression. The compression pressure was optimized to simultaneously produce a solid product. This product resisted breakage during normal shipping and facilitated rapid product mixing (less than two min).

EXAMPLE 2

Prior to opening a container containing particles of the above composition, the volume of a bone void to be repaired was determined. Based on the bone void, an appropriate volume of non-human animal blood was obtained, using a ratio of 0.75:1 blood or bone marrow aspirate:bone void volume. Appropriate volumes of liquid were added, as subsequently described, to obtain products of desired cohesive consistency (e.g. paste). As one example, per 1 cc dry particle volume, 0.75 ml whole blood was added to obtain a cohesive putty, or 0.85 ml whole blood was added to obtain a paste. As another example, per 1 cc dry particle volume, 0.75 ml bone marrow aspirate was added to obtain a cohesive putty, or 0.85 ml bone marrow aspirate was added to obtain a paste.

Immediately prior to implantation on an isolated bone, the liquid was mixed with the composition to obtain a paste of desired consistency. The bone void site was irrigated as needed and the paste was packed into the bone void. The site was sealed with surrounding soft tissue as needed, e.g., to close the wound and restore soft tissue configuration. Rigid fixation of the defect site stabilized the bone void.

It should be understood that the embodiments and examples described are only illustrative and are not limiting in any way. Therefore, various changes, modifications or alterations to these embodiments may be made or resorted to without departing from the spirit of the invention and the scope of the following claims.

What is claimed is:

1. A process for producing a bone growth composition comprising combining a fibrillar collagen component with an acidic calcium phosphate component to produce a mineralized collagen component, and creating particles of the mineralized collagen component, wherein the mineralized collagen component comprises the form of a crosslinked sponge prior to creating the particles, wherein creation of the particles includes milling.

2. The process of claim 1 wherein the mineralized collagen component comprises the form of a gel prior to creating the particles.

3. The process of claim 1 comprising adding an osteoinductive component to the composition.

4. The process of claim 3 wherein the osteoinductive component is added after the particles are formed.

5. The process of claim 1 wherein combining a fibrillar collagen component with an acidic calcium phosphate component to produce a mineralized collagen component further comprises preparing a collagen gel.

6. The composition of claim 5 further comprising lyophilizing the mineralized collagen compomnent.

7. The process of claim 1 wherein the acidic calcium phosphate is selected from the group consisting of monocalcium phosphate $[Ca(H_2PO_4)_2]$, calcium phosphate dibasic $[CaHPO_4]$, calcium pyrophosphate $[2CaO.P_2O_5]$, and combinations thereof.

8. The process of claim 7 wherein the acidic calcium phosphate comprises calcium phosphate dibasic $[CaHPO_4]$.

9. The process of claim 1 wherein collagen is dehydrothermally crosslinked.

10. A process for producing a bone growth composition comprising combining a fibrillar collagen component with an acidic calcium phosphate component to produce a mineralized collagen component, and creating particles of the mineralized collagen component, wherein the mineralized collagen component comprises the form of a crosslinked sponge prior to creating the particles, further comprising including the particles in a kit.

11. The process of claim 10 wherein the kit includes a device for mixing the particles with a fluid.

12. The process of claim 10 wherein the kit includes a receptacle for mixing the particles with a fluid.

13. A process for producing a bone growth composition comprising combining a fibrillar collagen component with an acidic calcium phosphate component to produce a mineralized collagen component, and creating particles of the mineralized collagen component, wherein the mineralized collagen component comprises the form of a crosslinked sponge prior to creating the particles, further comprising sizing the particles.

14. The process of claim 13 wherein the size of the particles is selected by sieving.

* * * * *